United States Patent
Ng et al.

(10) Patent No.: US 6,743,174 B2
(45) Date of Patent: Jun. 1, 2004

(54) ULTRASONIC DIAGNOSTIC IMAGING SYSTEM WITH AUTOMATICALLY CONTROLLED CONTRAST AND BRIGHTNESS

(75) Inventors: Gary Ng, Bothell, WA (US); Brian Hendee Smith, Woodinville, WA (US)

(73) Assignee: Koninklijke Philips Electronics N.V., Eindhoven (NL)

( * ) Notice: Subject to any disclaimer, the term of this patent is extended or adjusted under 35 U.S.C. 154(b) by 0 days.

(21) Appl. No.: 10/114,727

(22) Filed: Apr. 1, 2002

(65) Prior Publication Data

US 2003/0187353 A1 Oct. 2, 2003

(51) Int. Cl.[7] .................................................. A61B 8/00
(52) U.S. Cl. ........................................ 600/437; 73/631
(58) Field of Search ................................. 600/437, 438, 600/440, 441, 442, 443, 445–458, 459–471; 367/7, 11, 130, 138; 73/625, 626, 619–624, 630–633, 634–648; 128/916

(56) References Cited

U.S. PATENT DOCUMENTS

| | | |
|---|---|---|
| 4,356,731 A | 11/1982 | Mahony |
| 4,408,492 A | 10/1983 | Kossoff et al. |
| 4,662,380 A | 5/1987 | Riley |
| 4,852,576 A | 8/1989 | Inbar et al. |
| 5,394,750 A * | 3/1995 | Matzuk ........................ 73/629 |
| 5,456,255 A * | 10/1995 | Abe et al. .................... 600/443 |
| 5,482,045 A * | 1/1996 | Rust et al. ................... 600/437 |
| 5,579,768 A | 12/1996 | Klesenski |
| 6,102,859 A | 8/2000 | Mo |
| 6,120,446 A | 9/2000 | Ji et al. |
| 2003/0013959 A1 * | 1/2003 | Grunwald et al. .......... 600/437 |

OTHER PUBLICATIONS

Pye et al., "Clinical Trial of A New Adaptive TGC System for Ultrasound Imaging," The British Journal of Radiology, vol. 61, No. 726, 1988, pp 532–526.

* cited by examiner

Primary Examiner—Ali Imam
(74) Attorney, Agent, or Firm—W. Brinton Yorks, Jr.

(57) ABSTRACT

An ultrasonic diagnostic imaging system includes a predetermined TGC characteristic which is automatically selected or calculated at the initiation of a diagnostic procedure. An automatic TGC circuit analyzes current image data to calculate an adjustment to the predetermined TGC characteristic when activated by the clinician. The ultrasound system produces a displayed TGC curve which illustrates the predetermined TGC characteristic as modified by automatic adjustment and any manual refinement done by the clinician. In a preferred embodiment automatic TGC modification is accompanied by automatic overall gain and dynamic range adjustment to automatically optimize image quality.

25 Claims, 6 Drawing Sheets

ULTRASONIC DIAGNOSTIC IMAGING SYSTEM WITH AUTOMATICALLY CONTROLLED CONTRAST AND BRIGHTNESS

This invention relates to ultrasonic diagnostic imaging systems and, in particular, to ultrasonic diagnostic imaging systems in which image brightness and contrast is automatically controlled.

Ultrasound imaging is often used in the diagnosis of patients who complain of nonspecific abdominal pain To diagnose this symptom the clinician will image most or all of the major organs of the abdomen. This will produce twenty, thirty, or more images of different organs at different depths, and from different acoustic windows of the body. Consequently the ultrasonic echoes obtained by such scanning will have undergone varying levels of attenuation as the ultrasound beams and echoes traverse different paths through the body. The varying echo levels will result in images of differing brightness. When the clinician notices these varying image appearances, the first instinct is to adjust the ultrasound system controls to negate them. For instance, if the deepest portion of an image is unusually dark, the clinician will adjust the time gain compensation (TGC) setting to provide more gain in the image at greater depths. If the overall brightness of the image is too bright or too dark, the clinician will adjust the overall gain control dial. If the image is noisy, especially in fluid-filled regions such as the gall bladder, the clinician will adjust the dynamic range of the signal path or image processor. It would be desirable to alleviate this task of constant adjustment by providing an ultrasound system that will recognize these image variations and provide the needed compensation automatically, so that the variety of images acquired during a study will exhibit comparable image appearance.

In accordance with the principles of the present invention, an ultrasonic diagnostic imaging system is provided which automatically compensates for variations in brightness or contrast. In accordance with one aspect of the present invention, variations in brightness are compensated by computing offsets to a nominal TGC curve which will compensate for depth dependent attenuation, then applying the offsets to the TGC curve for subsequent images. In accordance with another aspect of the present invention, image dynamic range is analyzed by comparing measurements of a recent image to comparable measurements of a reference image, then adjusting the dynamic range of the image processing path in accordance with the noted differences. In accordance with still another aspect of the present invention, differences between the compression function used to reduce the dynamic range of a recent image and a reference image are used to automatically adjust overall system gain for substantially uniform image production by the ultrasound system.

Figure 1:
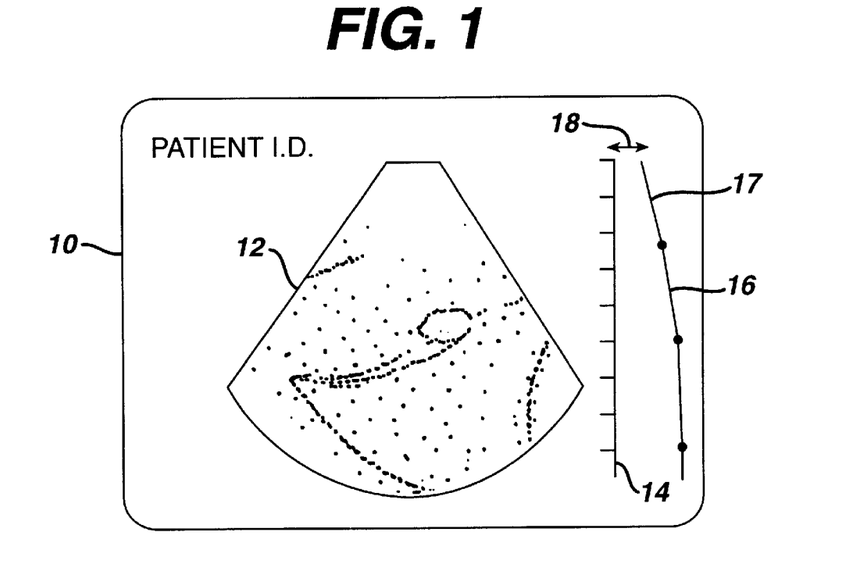
FIG. 1 illustrates an ultrasonic image display with a displayed TGC characteristic.

Referring first to FIG. 1, an ultrasonic image display 10 is shown. In the center of the display is the ultrasonic image 12 which shows the tissue structure or flow conditions of the patient being examined. In the upper left corner of the display is alphanumeric information concerning the patient and/or other characteristics of the examination being performed. To the right of the ultrasonic image 12 is a depth scale 14 aligned with the image, indicating the depth into the body to which the image extends. Usually the markers on the depth scale are calibrated in centimeters of depth.

Figure 2:
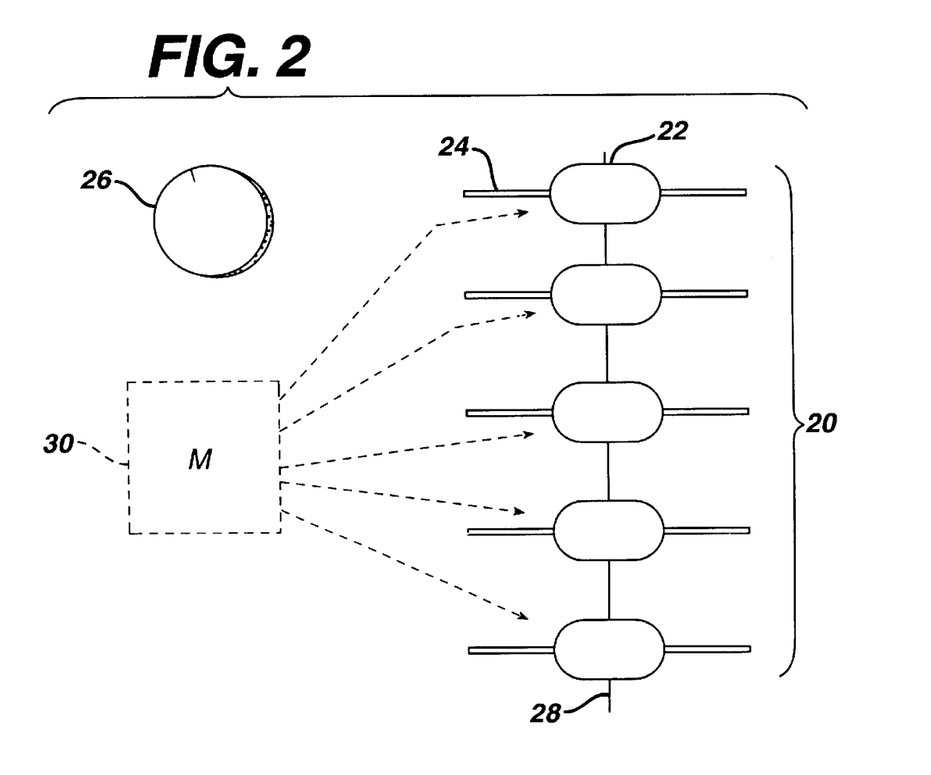
FIG. 2 illustrates the user controls of an ultrasound system which are used for varying the TGC characteristic and the overall system gain.

To the right of the depth scale 14 is a graphic representation 16 of the TGC characteristic. The TGC characteristic is shown as a sequence of line segments joined by dots on the display. The relative slope of each line segment indicates the variation in gain applied to the received echo signals over the depth covered by that segment. Setting an individual TGC switch, as shown in FIG. 2, will vary the slope of a respective line segment. Each line segment and its switch may have a predetermined, fixed depth over which it is effective, or the segments can be scaled in relation to the maximum depth of the particular image. An initial gain adjustment by a gain control 26 is used to offset the gain of the entire TGC characteristic, and causes the displayed characteristic 16 to move left or right as indicated by the arrow 18.

The slope of each segment of the TGC characteristic is set by one of the TGC switches 20 shown in FIG. 2. Conventionally the TGC switches are slide switches such as indicated by the first switch 22 which slides horizontally along the groove 24. There may be as few as four slide switches (for four TGC curve segments) or as many as sixteen or more switches (for sixteen segments). Switch 22 controls the gain over an initial depth portion of the image as indicated by the first segment 17 of the TGC characteristic 16. Moving slide switch 22 to the right will increase the gain more rapidly over this initial depth, and will cause the first line segment 17 on the display to slope more quickly to the right. Turning the gain control adjustment 26 will cause the gain over the full depth to vary, and the TGC characteristic to move to the right or left as indicated by the arrow 18. When all the TGC switches 20 are vertically aligned along the center line 28 as shown in FIG. 2, there will be no variation in gain over the depth of the image and the TGC characteristic 16 will appear as a straight vertical line over the full depth. If various ones of the TGC switches 20 are progressively moved to the right, a progressively sloping TGC characteristic 16 as shown in FIG. 1 will result.

In an entirely manual TGC system of the prior art, the clinician will set the switches manually for the type of anatomy being diagnosed and the attenuation characteristics encountered. Each time a new portion of anatomy is viewed or a different depth of image is selected, it may be desirable to change the TGC switch settings to produce a more diagnostic image. This purely manual approach to TGC control is improved by the arrangement described in U.S. Pat. No. 5,482,045, in which the ultrasound system automatically invokes a predetermined, optimized TGC characteristic at the start of an exam. The TGC characteristic is stored in or calculated by the ultrasound system at the start of an exam and is automatically invoked and displayed as TGC curve 16. The TGC characteristic can be optimized in consideration of any applicable diagnostic parameters, such as the image depth or the probe being used. In a preferred embodiment the TGC characteristic is optimized for the type of exam being performed. One curve is used for diagnosing the liver, another for diagnosing a fetus, and a third curve may be invoked for a cardiac exam. When the clinician manipulates the ultrasound system controls to select the type of exam being performed, the system assigns the appropriate TGC characteristic. This capability is referred to as "tissue specific" imaging.

When the ultrasound system assigns an optimal starting TGC characteristic, any manual adjustment of the slide switches is generally minimal. The tissue specific characteristic is set for the general range of patient conditions for the particular exam, and it is generally only necessary for the clinician to provide some fine tuning adjustments with the slide switches 20. Thus, the positions of the slide switches after adjustment will generally be only slightly offset from their nominal center positions. When the slide switches are all centered as shown in FIG. 2, the ultrasound system is using the predetermined TGC curve without alteration. The offset positions of the switches thus represent adjustments made to the predetermined TGC curve. This is different from a purely manual system, in which the positions of the switches represent the full TGC curve; when the switches are all centered, there is no TGC, no depth-dependent gain applied to the received echo signals. In both cases, the displayed TGC curve 16 illustrates the full TGC characteristic applied to the received echo signals.

If it is desirable for the physical positions of the switches 20 to constantly indicate the shape of the TGC characteristic 16 rather than variation from a predetermined setup TGC characteristic as described above, the switches can be motor controlled by a motor 30 as indicated in FIG. 2. When the user selects a given procedure and the ultrasound system sets up the preferred TGC characteristic for the selected procedure, the motor 30 is commanded to automatically move the switches 20 to physical positions corresponding to the slopes of the segments of the TGC characteristic 16. The switches 20 would move under motor control from their previous alignment to the alignment representing the TGC characteristic. Thereafter the user would manually adjust the switches to customize the predetermined setup TGC characteristic for the acoustical conditions of the particular patient's anatomy, as described above, and both the displayed TGC curve 16 and the physical alignment of the switches would constantly illustrate the full TGC characteristic.

In accordance with a preferred embodiment of the present invention, the gain control 26 is automated to operate in conjunction with a nominal gain setting that is predetermined for the particular exam being conducted. When the type of exam (or probe type, or image depth, or other diagnostic variable) is chosen, the ultrasound system automatically invokes a predetermine level of overall gain. Adjustment of the gain control 26 is then generally needed only to make fine adjustments to the predetermined gain level.

Figure 3:
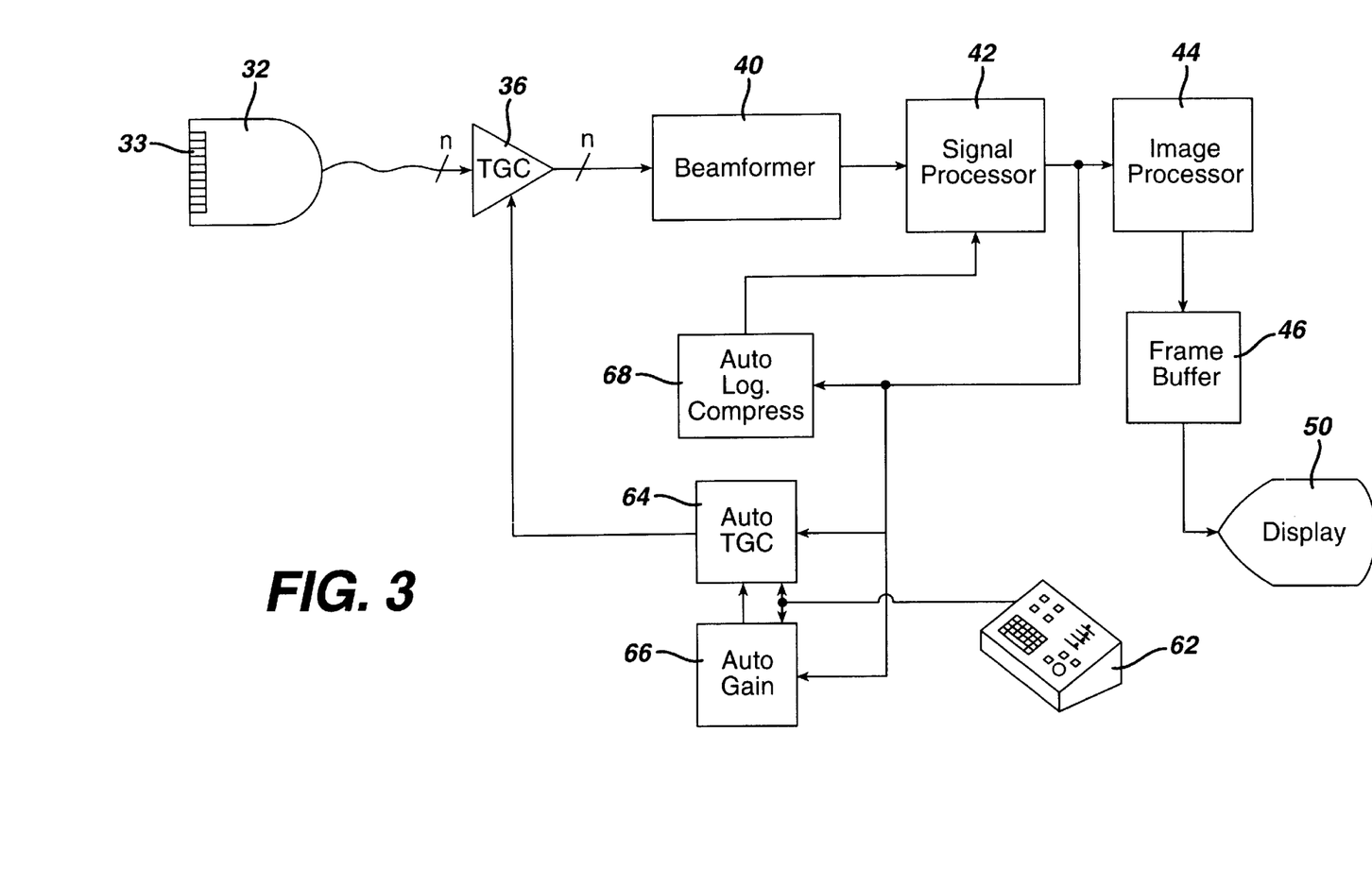
FIG. 3 illustrates in block diagram form an ultrasonic diagnostic imaging system constructed in accordance with the principles of the present invention.

An ultrasound system constructed in accordance with the principles of the present invention is shown in block diagram form in FIG. 3. A probe 32 with an array transducer 33 transmits ultrasonic waves under control of a beamformer 40 as steered and focused beams which scan the region of the body being diagnosed. Echoes returned from the transmitted beams are received by the transducer elements and coupled over n conductors of a cable to the inputs of n TGC amplifiers 36, one of which is represented in the drawing.

The amplified echoes are digitized and coupled over n conductors to the receive channels of the beamformer 40. The echoes from the active elements of the receiving aperture are delayed and combined in the beamformer to form received scanlines of coherent echo signals. The beamformed echoes undergo processing in a signal processor 42, which may include processes such as filtering, harmonic separation, quadrature demodulation, log compression, detection, or Doppler processing. The processed echo signals are then coupled to an image processor 44, where they are arranged into the desired image format. The image processor may include a scan converter which processes sector scanlines received in an R-θ spatial orientation into Cartesian coordinates. The image processor may also overlay or combine tissue and flow image portions or produce a three dimensional rendering of a volumetric region of the body being scanned. The processed image is stored at least temporarily in a frame buffer 46 from which the image is acquired for display on an image display 50.

In accordance with the principles of the present invention the ultrasound system includes an auto TGC processor 64 which operates to automatically control the depth dependent gain applied to received scanline signals as described below. An auto gain circuit 66 is provided to automatically set up a gain which is constant with depth, as described below. In the illustrated embodiment the gain of the auto gain circuit is applied as a constant offset to the TGC gain through a single TGC amplifier 36, although separate gain control circuits can be used for the two functions. The auto TGC processor and auto gain circuit receive inputs from a user operated control panel 62, through which the user can select a diagnostic procedure that leads to the automatic selection of an optimized predetermined TGC characteristic and overall gain setting, and through which the user can fine tune and adjust the TGC curve and gain automatically set up by the ultrasound system. An auto log compression processor 68 provides an automatically determined log compression function for the log compression circuit in the signal path of the signal processor 42, the operation of which is more fully described below.

Figure 4A:
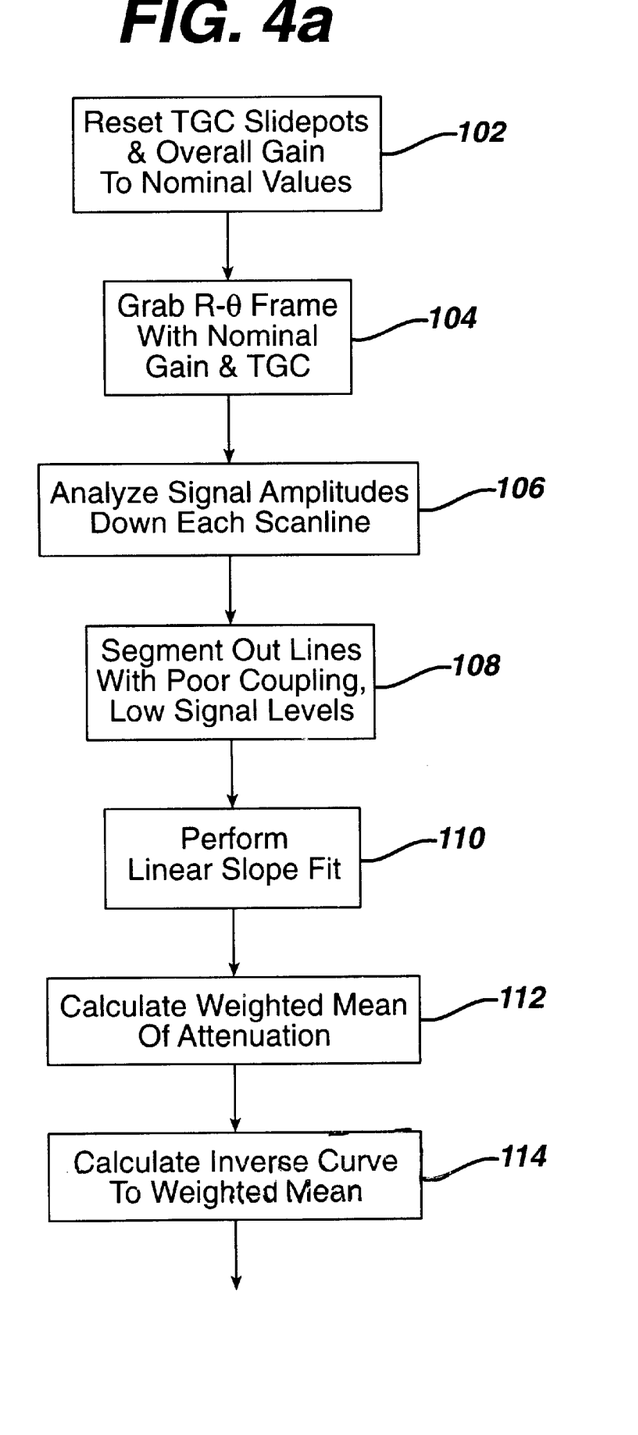
FIGS. 4a–4c are a flowchart illustrating a method for automatically adjusting the TGC characteristic, the gain, and the dynamic range of an ultrasound system in accordance with the principles of the present invention.
Figure 4B:
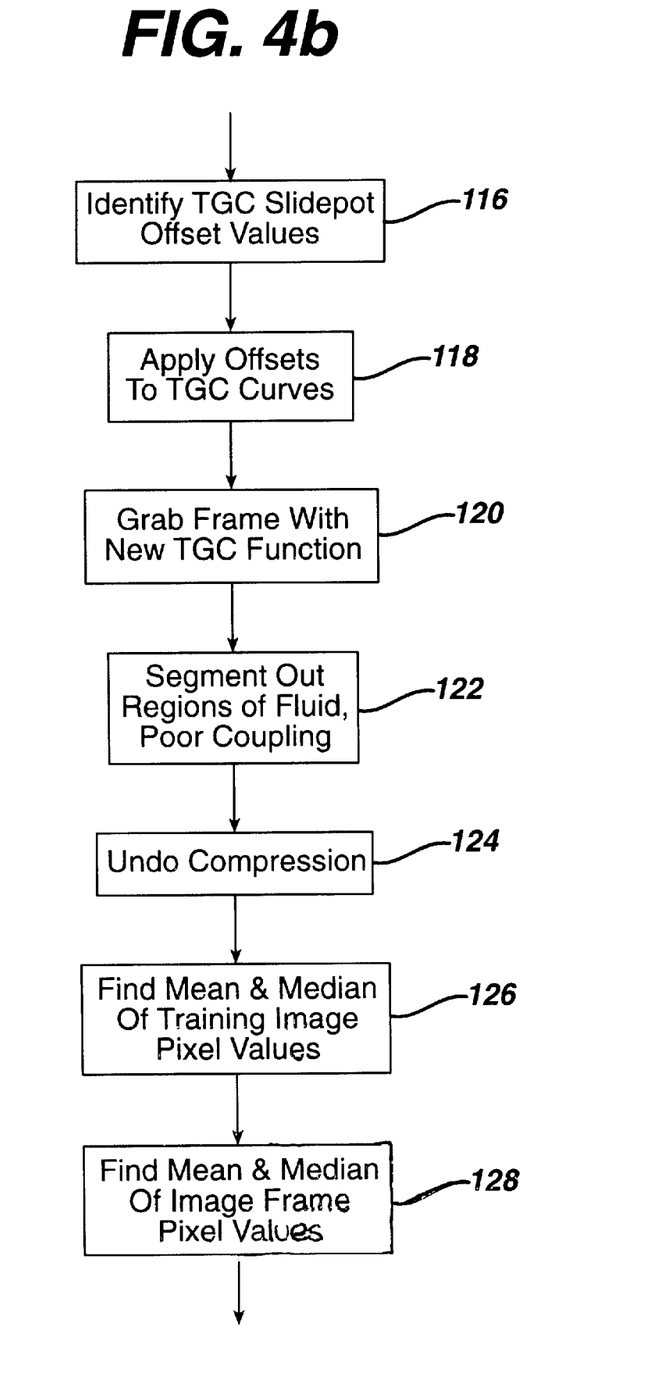
Figure 4C:
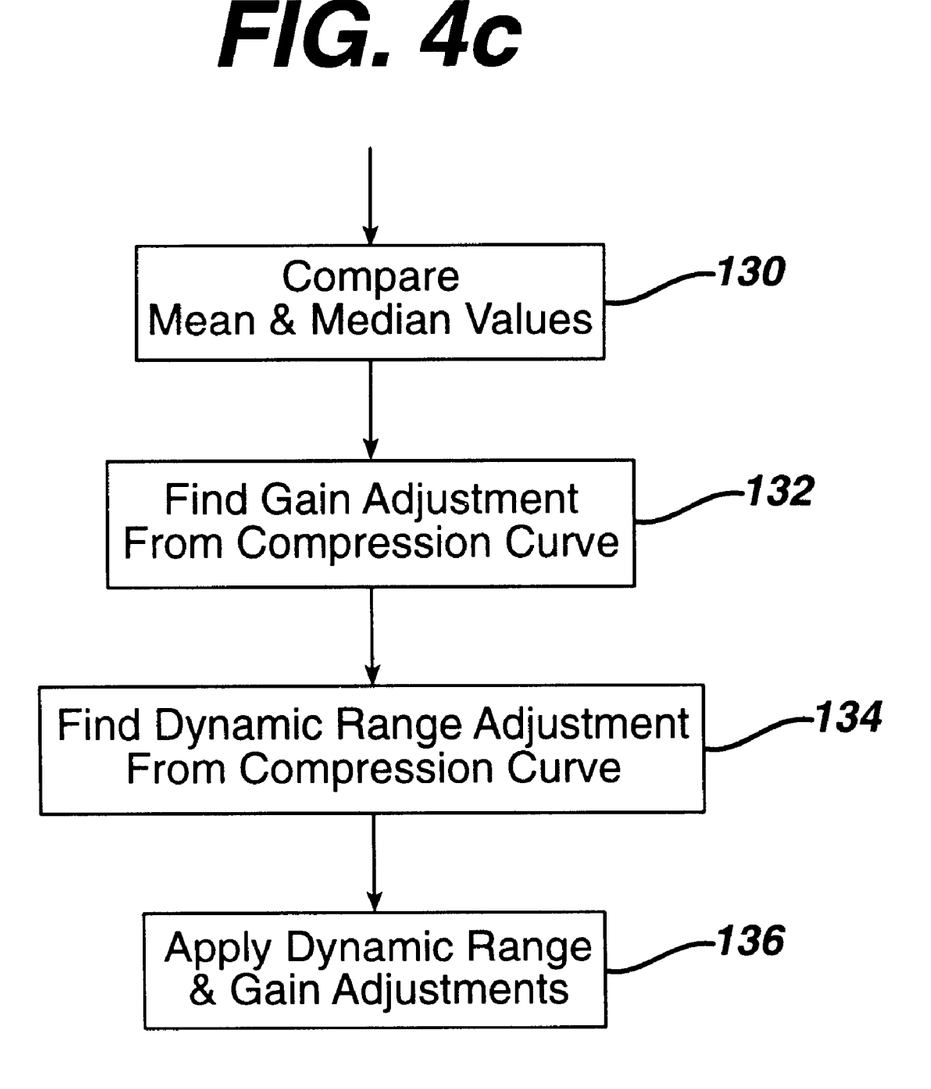

FIGS. 4a–4c are a flowchart illustrating a method for automatically adjusting the TGC characteristic, the gain, and the dynamic range of an ultrasound system in accordance with the principles of the present invention. This automatic control can be set up to operate continuously, or to operate only upon command. For instance, the user may be viewing an image 12 which appears too dark, too light, or exhibits wide contrast variability. In that case the user can depress a control on the control panel 62 to cause the automatic TGC, gain, or dynamic range functions to automatically adjust the current image (if buffered) or to provide automatic adjustment to subsequent images (in real time operation.) In a preferred embodiment, the user depresses the control on the control panel or a display screen to activate one cycle of automatic TGC, gain and compression curve optimization. The characteristics thus calculated are used to process images until the control is depressed again, at which time a new, updated set of characteristics is calculated, which then is used to process subsequent images. The characteristic set by this automatic optimization can be reset, in which case the system is reset to processing subsequent images with only the preprogrammed TGC, gain and compression characteristics. The gain, TGC and compression controls are also restored to their original behavior prior to automatic optimization.

In a preferred embodiment of the present invention the ultrasound system stores TGC characteristics (or TGC characteristic parameters from which TGC characteristics can be determined) which are specially designed for different diagnostic exams. When the user starts a particular exam, the ultrasound system will invoke the preferred TGC characteristic 16 for that exam type as an initial TGC function. The user may then adjust or fine tune this initial characteristic for the acoustic conditions presented by the particular patient being examined.

When the processing of the present invention is invoked, either automatically or by user command, the manually set TGC control and gain values are reset to their nominal values (step 102). If the TGC slidepots 20 are motor controlled as described above, the slidepots will be motor-driven to positions corresponding to the system-predetermined TGC characteristic. At this point, the ultrasound system is producing images which are a function just of the optimized predetermined TGC characteristic and of the predetermined initial gain level.

With the system-selected TGC and gain applied to the imaging signal path, an image frame is acquired (step 104). The image frame is preferably acquired prior to scan conversion processing, when it is still in the R-θ format. This enables the auto TGC function to operate on the received echo data without the effects of image processing such as interpolated pixel values.

Figure 5:
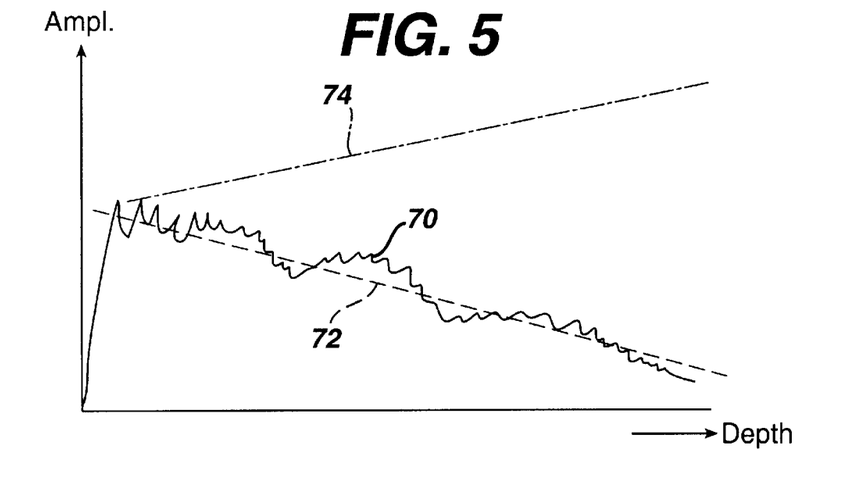
FIG. 5 are curves illustrating a method for automatically adjusting a TGC characteristic.

The auto TGC function is performed on the R-θ image, which begins by analyzing the signal amplitudes down each scanline (step 106). With no manual TGC variation, the signal amplitudes may exhibit a general decline with depth, as represented by the amplitude plot 70 of FIG. 5. Next, scanlines which exhibit poor coupling or low signal levels are discarded (step 108). For example, the scanlines at the lateral periphery of an image acquired with a curved array probe may be noisy or indistinct due to poor coupling with the patient's body at the periphery of the transducer array. Since such lines are not generally representative of the image as a whole, they are not used in the automated process. Also, samples within each scan line with low signal levels may also be discarded. Next, a linear slope fit is performed (step 110) on the retained data. FIG. 5 illustrates an example of a dashed line 72 which is fitted to the general slope of the amplitude data of scanline 70. While this linear slope fit may be applied to the scanlines after they have undergone signal processing, preferably it is performed prior to log compression or with the log compression undone, so that the process is operating on data with a linearly varying dynamic range. Alternatively, it is possible the fit a sequence of line segments to the varying slope of the amplitude data as described in U.S. Pat. No. 4,852,576. However, it has been found that a single line fit will provide the desired level of automatic optimization when combined with the optimized predetermined TGC characteristic, as the predetermined characteristic will generally exhibit segment-to-segment variation.

When a linear slope has been fitted to the depth-dependent attenuation characteristic of each scanline in the image frame, these slopes are combined into a single slope value for the image. A preferred way to combine the individual scanline values is to calculate a weighted mean of the attenuation estimates (step 112.) One way to do this is to sum the amplitude values for each line, then weight the contribution of each scanline in proportion to the relation of the sum for that scanline to the total sum of all scanlines. This will effectively cause image regions with good echo signal content to contribute more to the final result than do regions of little or no signal content. A single linear slope value α is thus produced for the image.

Figure 6:
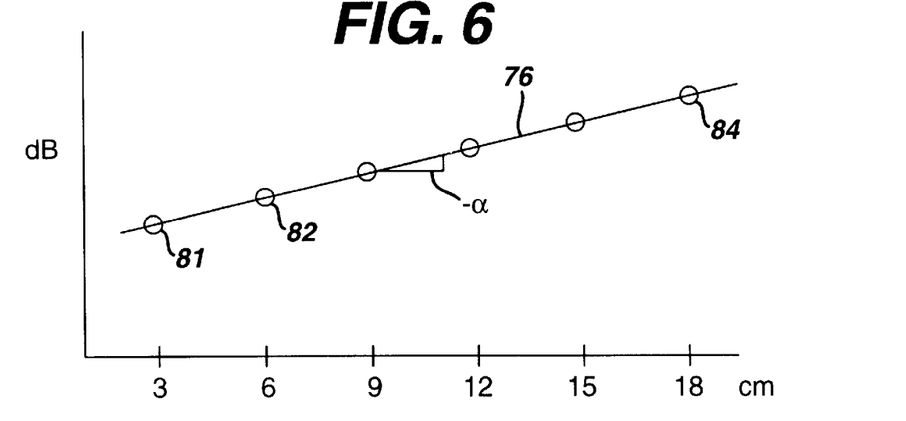
FIG. 6 illustrate calculated TGC slidepot offsets.

In the next step, an inverse curve to the weighted mean slope is calculated (step 114.) For example, if the linear slope α was represented by dashed line 72, its inverse curve would be dashed and dotted curve 74, which slopes upward inversely in relation to the downward slope of dashed line 72. In the next step, TGC offset values are identified from the inverse curve (step 116.) For example, FIG. 6 illustrates an inverse curve 76 with an upward slope $-\alpha$ (where α is referenced to the horizontal) which has an increasing gain (dB) with increasing depth (cm). Located along the curve 76 at depth increments corresponding to those of the TGC slidepot depth increments are discrete gain values shown as circles 81, 82, . . . 84. These identified gain values are applied to the corresponding segments of the optimized predetermined TGC characteristic 16 (step 118.) Preferably, the values are applied to the preset TGC characteristic initially chosen by the ultrasound system for the exam. This will effectively adjust the system-provided TGC characteristic by providing it with a calculated linear tilt. The new depth-dependent TGC values are applied to the TGC amplifiers 36 and subsequent images are produced with this automatically corrected TGC characteristic.

In some applications it may be desirable to add a predetermined bias to the slope factor $-\alpha$ to account for certain user preferences or how images appear in certain applications. The final slope factor would then be of the form $(-\alpha+\text{bias})$. The bias is preferably adjusted per application or 2D imaging setting to address amplitude variations with depth that are unique for that application, and to accommodate cases in which a visually uniform image actually results when far field acoustic signals are slightly attenuated.

The displayed TGC curve 16 is modified as necessary to correspond to the full TGC characteristic, that is, the initial system-provided characteristic as modified by the calculated linear tilt adjustment. In a system with unmotorized slidepots 20 the physical locations of the slides at their current locations, whatever they may be, represent no manual change to the displayed TGC characteristic. The manual slidepots may be adjusted by the clinician as desired to provide manual additional adjustment to the TGC characteristic which has been automatically calculated by the auto TGC circuit, and the displayed TGC curve 16 will move in correspondence to any adjustments.

The ultrasound system then performs automatic gain and log compression determination. This process begins by acquiring an image frame which has been processed with the automatically determined TGC function described above (step 120.) Alternatively, instead of acquiring a new image frame with the automatically determined TCG characteristic, the frame used in the auto TGC process can be processed by applying the new TGC gain values to each scanline of the frame. Next, regions of the image with poor signal content, such as regions where fluid is present or regions where coupling is poor, are eliminated. For example, consider a range of grayscale pixel values extending from 0 (darkest) to 255 (brightest). Regions of poor signal content may be eliminated by excluding from processing all values from 0–20 or 0–50, for instance. With poor signal levels removed, the log compression of the image, if present is undone (step 124.) This may be performed by a lookup table which is the reverse of that used to log compress the image data.

The data of the selected image is now processed in comparison with reference data. A preferred source of reference data is an image which the user feels is a desirable image, referred to herein as a training image. The training image may alternatively be supplied with the ultrasound system, and preferably chosen for the type of exam being performed. The training image, whatever its source, is then processed by calculating the mean and median of the pixel values in the image without the effect of log compression (step 126.) This will produce an average uncompressed pixel value and a median uncompressed pixel value. This processing may be done in the factory by providing the ultrasound system with precalculated mean and median training pixel values.

The same processing is now performed on the selected image. With the grayscale pixel values now in a linear format, the mean and median values of the pixel values of the selected image are calculated (step 128.) This will produce an average uncompressed pixel value and a median uncompressed pixel value for the selected image. The mean and median values of the selected image are compared with the mean and median values of the training image (step 130), and the comparison is used to find a new compression curve from which are derived new gain and compression parameters (steps 132, 134). These new values are applied as gain adjustments to the TGC amplifiers 36 and as an adjusted log compression function for the signal processor 42.

This processing may be understood by considering the following example. Ultrasound echo data is often digitized with 16–18 bit precision, which can give a data range of over 100 dB. For purposes of display, the data is mapped to an 8-bit gray level value, which corresponds to under 50 dB of dynamic range. The data is eventually displayed on an image display 50 and observed with the human visual system, which has a very poor ability for differentiating gray levels in a 100 dB range. To map the 18-bit echo data into an 8-bit value, the data is log-compressed. The compression process maps the output values into input values through the equation $$\text{output} = a \cdot (\log_{10}(\text{input}) - b)$$

Figure 7:
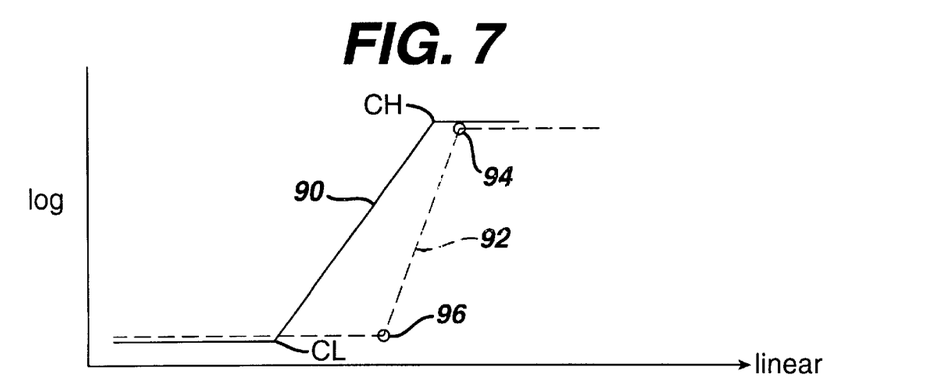
FIG. 7 illustrates the use of a compression curve for adjusting gain and dynamic range in accordance with the principles of the present invention.

The output value is rounded to an 8-bit value, and clipped to be within the range 0 to 255. The compression map can be characterized by two clip points, CL and CH, which characterize the minimum and maximum input values that will be clipped. When the output value is plotted as a function of the input value in a log-linear format, we get a piecewise linear function such as that represented by the function 90 in FIG. 7. The parameters a and b of the compression transfer function can be calculated from the clip points, CL and CH, through the relationship $$a = \frac{255}{\log_{10}\left(\frac{CH}{CL}\right)}$$

$$b = \log_{10}(CL)$$

Estimates of the clip points, $CH_i$ and $CL_i$ for training image i can also be calculated from the image data itself. This is done by calculating the uncompressed mean and median pixel values of training image i and various weighting coefficients, w1, w2, and w3, that relate these mean and median values to the clip points. These weighting coefficients are calculated by minimizing the mean squared error between the estimated clip points, $CH_i$ and $CL_i$ and the desired compression function with clip points $CH^o_i$ and $CL^o_i$ over a set of n training images. These weighting coefficients calculated from the training images were then used with the uncompressed mean value and the uncompressed median value of the selected image to establish a new compression function for the selected image. This new compression function is represented by the dashed line 92 in FIG. 7. Application of the compression function calculated from parameters w1, w2, and w3, to a selected image results in distributing the image amplitude levels such that they more closely match an image that had been log compressed with a function characterized by clip points $CH^o_i$ and $CL^o_i$. The CH and CL clip points are shown at 94 and 96. The horizontal (linear) differences of the two functions 90, 92 provide a gain adjustment: moving the selected image function to the left to align with the training image function is an addition of gain and moving the function to the right for alignment calls for a reduction in gain. Likewise, the change of slope between the clip points which is necessary to align one function to the other represents a change in dynamic range. The gain adjustment is applied to the TGC amplifier by way of the auto TGC processor and the dynamic range adjustment is applied to the log compression circuit of the signal processor.

As in the case of the TGC control, in a preferred embodiment the gain value applied to the amplifier is a combination of a system predetermined nominal gain value as modified by the automatically determined gain adjustment, and the dynamic range characteristic used is a combination of a system predetermined nominal dynamic range characteristic as modified by the automatically determined dynamic range adjustment. If the user is dissatisfied with the image after these automatic adjustments have been made, the user can manually adjust the TGC controls 20, the gain control 26, or the dynamic range control (not shown) on the ultrasound system to further refine the image. Both the gain and dynamic range can be reset to the nominal values if desired.

What is claimed is:

1. In an ultrasonic diagnostic imaging system which uses a system-predetermined TGC characteristic for an imaging procedure, a method for optimizing the TGC characteristic comprising:

obtaining an ultrasound image which has been produced in response to the system-predetermined TGC characteristic;

analyzing the ultrasound image data with a system processor to produce an adjustment to a TGC characteristic relative to that provided by the system-predetermined TGC characteristic; and producing an ultrasound image which has been produced in response to the system-predetermined TGC characteristic as modified by the TGC characteristic adjustment.

2. The method of claim 1, wherein obtaining comprises obtaining a plurality of scanlines of echo amplitude data extending over a depth of image.

3. The method of claim 2, wherein analyzing further comprises fitting a line with a slope which approximates the variation of echo amplitude with depth.

4. The method of claim 1, wherein analyzing further comprises analyzing ultrasound image data prior to scan conversion to Cartesian coordinates.

5. The method of claim 4, wherein analyzing further comprises analyzing ultrasound image data which is in R-θ format.

6. The method of claim 1, further comprising obtaining a system-predetermined TGC characteristic from a data storage device of the ultrasound system.

7. The method of claim 1, further comprising obtaining a system-determined TGC characteristic by system computation using imaging procedure parameters.

8. The method of claim 7, wherein obtaining a system-predetermined TGC characteristic by system computation comprises computing a TGC characteristic using at least one of a probe parameter, image depth, or exam type.

9. In an ultrasonic diagnostic imaging system which uses a system-predetermined TGC characteristic for an imaging procedure, a method for optimizing the TGC characteristic comprising:

obtaining an ultrasound image which has been produced in response to the system-predetermined TGC characteristic;

analyzing the ultrasound image data to produce an adjustment to a TGC characteristic relative to that provided by the system-predetermined TGC characteristic; and producing an ultrasound image which has been produced in response to the system-predetermined TGC characteristic as modified by the TGC characteristic adjustment, wherein obtaining further comprises obtaining an ultrasound image which has been produced to the exclusion of gain control from manual TGC adjustment.

10. In an ultrasonic diagnostic imaging system which uses a system-predetermined TGC characteristic for an imaging procedure, a method for optimizing the TGC characteristic comprising:

obtaining an ultrasound image which has been produced in response to the system-predetermined TGC characteristic;

analyzing the ultrasound image data to produce an adjustment to a TGC characteristic relative to that provided by the system-predetermined TGC characteristic; and producing an ultrasound image which has been produced in response to the system-predetermined TGC characteristic as modified by the TGC characteristic adjustment, further comprising displaying a TGC characteristic which is a composite of the system-predetermined TGC characteristic and the TGC characteristic produced by the analyzing step.

11. The method of claim 10, further comprising manually adjusting the displayed composite TGC characteristic.

12. In an ultrasonic diagnostic imaging system which uses a system-predetermined TGC characteristic for an imaging procedure, a method for optimizing the TGC characteristic comprising:

obtaining an ultrasound image which has been produced in response to the system-predetermined TGC characteristic;

analyzing the ultrasound image data to produce an adjustment to a TGC characteristic relative to that provided by the system-predetermined TGC characteristic; and producing an ultrasound image which has been produced in response to the system-predetermined TGC characteristic as modified by the TGC characteristic adjustment, further comprising continuing to produce ultrasound images in response to a the system-predetermined TGC characteristic as modified by a given TGC characteristic adjustment until one of a) the system is actuated by the user to produce a new TGC adjustment; or b) the given TGC characteristic adjustment is reset.

13. The method of claim 12, further comprising manually adjusting a system-predetermined TGC characteristic as modified by a given TGC characteristic adjustment at any time.

14. In an ultrasonic diagnostic imaging system, a method for optimizing an ultrasonic image comprising:

automatically optimizing the TGC characteristic used to process the received echo data; and automatically optimizing the dynamic range used to process the received echo data, wherein the system stores a predetermined dynamic range characteristic, and further comprising:

continuing to produce ultrasound images in response to a given automatically optimized dynamic range determination until one of:

a) the system is actuated by the user to determine a new automatically optimized dynamic range determination; or b) the dynamic range is reset to the predetermined dynamic range characteristic.

15. In an ultrasonic diagnostic imaging system, a method for optimizing an ultrasonic image comprising:

automatically optimizing the TGC characteristic used to process the received echo data; and automatically optimizing the dynamic range used to process the received echo data;

further comprising:

automatically optimizing the overall gain applied to the received echo data, wherein the system stores a predetermined overall gain value, and further comprising:

continuing to produce ultrasound images in response to a given automatically optimized gain determination until one of:

a) the system is actuated by the user to determine a new automatically optimized gain determination; or b) the gain is reset to the predetermined overall gain value.

16. An ultrasonic diagnostic imaging system comprising:

means for producing a TGC characteristic using data stored on the ultrasound system;

an image storage device which stores images produced by a system-produced TGC characteristic;

an auto TGC processor which analyzes images produced by a system-produced TGC characteristic to produce a TGC characteristic adjustment; and a gain control circuit responsive to a system-produced TGC characteristic as modified by a TGC characteristic adjustment which produces echo data with gain controlled as a function of depth.

17. The ultrasonic diagnostic imaging system of claim 16, wherein the TGC characteristic producing means comprises a storage device which stores parameters of a TGC characteristic.

18. The ultrasonic diagnostic imaging system of claim 16, wherein the TGC characteristic producing means comprises a processor which produces a TGC characteristic in response to an imaging procedure parameter.

19. The ultrasonic diagnostic imaging system of claim 18, wherein the imaging procedure parameter includes at least one of clinical exam type, imaging depth, or probe type.

20. The ultrasonic diagnostic imaging system of claim 16, wherein the TGC characteristic adjustment comprises a linear slope adjustment to a gain vs. depth TGC characteristic.

21. The ultrasonic diagnostic imaging system of claim 16 further comprising a display which displays a system-produced TGC characteristic as modified by a TGC characteristic adjustment produced by the auto TGC processor.

22. An ultrasonic diagnostic imaging system comprising:

means for producing a TGC characteristic using data stored on the ultrasound system;

an image storage device which stores images produced by a system-produced TGC characteristic;

an auto TGC processor which analyzes images produced by a system-produced TGC characteristic to produce a TGC characteristic adjustment; and a gain control circuit responsive to a system-produced TGC characteristic as modified by a TGC characteristic adjustment which produces echo data with gain controlled as a function of depth, further comprising a display which displays a system-produced TGC characteristic as modified by a TGC characteristic adjustment produced by the auto TGC processor, and further comprising a manual TGC characteristic control, wherein the display displays a system-produced TGC characteristic as modified by a TGC characteristic adjustment produced by the analysis software as modified by a manual TGC characteristic adjustment.

23. An ultrasonic diagnostic imaging system comprising:

an image storage device which stores images produced in response to a TGC characteristic;

an auto TGC processor which analyzes images produced in response to the TGC characteristic to produce a TGC characteristic adjustment; and an auto log compression processor which analyzes images to determine a compression curve adjustment; and a signal path responsive to the auto TGC processor and the auto log compression processor which produces images in response to the TGC characteristic adjustment and the compression curve adjustment.

24. An ultrasonic diagnostic imaging system comprising:

an image storage device which stores images produced in response to a TGC characteristic;

an auto TGC processor which analyzes images produced in response to the TGC characteristic to produce a TGC characteristic adjustment; and an auto log compression processor which analyzes images to determine a compression curve adjustment; and a signal path responsive to the auto TGC processor and the auto log compression processor which produces images in response to the TGC characteristic adjustment and the compression curve adjustment, further comprising:

an auto gain processor which analyzes images to determine an overall gain adjustment, wherein the signal path is further responsive to the overall gain adjustment.

25. The ultrasonic diagnostic imaging system of claim 24, further comprising manual controls which may be operated to manually adjust a TGC characteristic, overall gain, and a compression characteristic.

* * * * *